(12) United States Patent
Crockett (10) Patent No.: US 8,392,216 B2
(45) Date of Patent: Mar. 5, 2013

(54) ASSOCIATION OF DATA ENTRIES WITH PATIENT RECORDS, CUSTOMIZED HOSPITAL DISCHARGE INSTRUCTIONS, AND CHARTING BY EXCEPTION FOR A COMPUTERIZED MEDICAL RECORD SYSTEM

(75) Inventor: Mark D. Crockett, Naperville, IL (US)

(73) Assignee: Picis, Inc., Wakefield, MA (US)

( * ) Notice: Subject to any disclaimer, the term of this patent is extended or adjusted under 35 U.S.C. 154(b) by 1656 days.

(21) Appl. No.: 11/182,497

(22) Filed: Jul. 15, 2005

(65) Prior Publication Data

US 2006/0036472 A1  Feb. 16, 2006

Related U.S. Application Data

(60) Provisional application No. 60/588,651, filed on Jul. 16, 2004.

(51) Int. Cl.
G06Q 10/00 (2012.01)
(52) U.S. Cl. .................. 705/3; 705/2; 707/104
(58) Field of Classification Search .............. 705/3
See application file for complete search history.

(56) References Cited

U.S. PATENT DOCUMENTS 5,664,109 A * 9/1997 Johnson et al. ............... 705/2
5,867,821 A * 2/1999 Ballantyne et al. ........... 705/2
6,502,756 B1   1/2003 Fahraeus
7,013,298 B1 * 3/2006 De La Huerga ............. 707/3
2002/0077865 A1 * 6/2002 Sullivan ....................... 705/3

FOREIGN PATENT DOCUMENTS

WO   WO0241761   5/2002

OTHER PUBLICATIONS

The Pen, Anoto Group AB, printed from http://www.anoto.com/?id=908 on Nov. 20, 2009, 1 page.

* cited by examiner

Primary Examiner — Hiep V Nguyen
(74) Attorney, Agent, or Firm — Wolf, Greenfield & Sacks, P.C.

(57) ABSTRACT

Apparatus and a method for associating an electronic patient record with the corresponding patient are described. A data processor accesses a patient record not associated with a unique person and compares the patient identification data to corresponding data in a known patient record to identify a set of likely matching patients. An input is provided for selecting a matching patient. Also disclosed is apparatus for providing customized patient discharge instructions relating information in the electronic patient record to patient-specific discharge instructions. A data processor inserts the patient specific instructions into draft instructions, thereby producing patient-specific discharge instructions. An updated version of charting by exception is disclosed, using macros to positively record data on a medical record that is not specifically marked on a template by the attending medical professional. Also described is an apparatus for translating a visual documentation language, communicating specific medical concepts in a highly compact form, to clinically relevant English, enhancing the usability of a pen/digital camera combination for data entry.

22 Claims, 5 Drawing Sheets

```
ELECTRONIC MEDICAL RECORD                    ⎫ —122
Chief                                        ⎪
Complaint         Chest Pain         — 82
Clinician ID      Lois Lane, MD.     — 84
Patient ID        John Smith         — 86
Gender            Male               — 88
Age               37                 — 90
Height (in.)      71                 — 92
Weight (lb.)      NORMAL             — 94
Blood Pressure    Normal             — 96
Pulse/min         Normal             — 98
Temperature (°F)  Normal             — 100
Heart Beat        Irregular          — 102
Lungs             CLEAR              — 104
                  not applicable     — 108
Pregnancy Test
```

FIG. 7

ASSOCIATION OF DATA ENTRIES WITH PATIENT RECORDS, CUSTOMIZED HOSPITAL DISCHARGE INSTRUCTIONS, AND CHARTING BY EXCEPTION FOR A COMPUTERIZED MEDICAL RECORD SYSTEM

CROSS-REFERENCE TO RELATED APPLICATIONS

Priority is claimed from provisional application U.S. Ser. No. 60/588,651, filed Jul. 16, 2004. The entire specification and all the claims of the provisional application referred to above are hereby incorporated by reference to provide continuity of disclosure. The following patent applications address related subject matter: U.S. application Ser. No. 09/928,130, filed Aug. 10, 2001, published as PCT appl. WO 0 241 761 A2; and U.S. application Ser. No. 10/000,879, filed Nov. 2, 2001, published as U.S. Publ. Appl. 2002/077865. The listed applications are incorporated here by reference.

STATEMENT REGARDING FEDERALLY SPONSORED RESEARCH OR DEVELOPMENT

None.

BACKGROUND OF THE INVENTION

Medical emergency room patient record software has been developed to ease the collection, processing, and use of medical records in various settings, such as a hospital emergency room. One problem with such software is the need to train and motivate physicians and other medical staff to promptly and accurately enter patient data into a system running the software.

Physicians have been trained to make paper records of their work, often using a pen and a blank sheet of paper, a preprinted form having blanks for recording information, or a dictating machine to record their initial notes. The physicians subsequently need to follow up or be followed up in some fashion to translate their informal notes into electronic records on a permanent recording system.

It is often difficult to train and motivate physicians accustomed to making paper notes to enter their original notes directly on the medical charting software, as by using a computer keyboard, a personal digital assistant (PDA), a tablet computer, or other electronic media. One value of the present invention is to allow a physician to enter paper notes in the traditional fashion, in a way that makes an immediate, permanent, electronic record entered in the medical charting software.

Systems have been developed for automatically converting handwritten informal notes, as on a preprinted form or even a plain sheet of paper, into formatted electronic records. For example, Anoto has developed text and image recording forms based on a sheet of paper with a subtle grid with a pattern of dots or "glyphs" printed on it. The pattern is different on each part of the paper, with a high degree of resolution, so an electronic image of a particular portion of the paper can be identified as such by decoding the pattern recorded as part of the electronic image.

The paper is written upon using a pen that includes a digital camera to frequently record (generally many times per second) where the pen is, with respect to the paper. The location of the pen is determined by recording an image of a small portion of the grid of glyphs in the vicinity of the pen, and immediately or later transmitting the images to a computer system that reads the glyphs and determines. the location of the pen on the grid from moment to moment. The computer system can determine what is written and where on the page it is written by processing the photographs, as by reading the handwriting reconstructed from the positions and movements of the pen. Alternatively, the reconstructed handwritten entries can be stored as images, as in a portable document format (.pdf), tif, or other image file. See e.g. U.S. Pat. No. 6,502,756.

One currently available physical arrangement of the system is that the pen is cordless, it saves a record of the marks on a page when the "magic box" on the page is marked, and when the pen is inserted in a cradle or holder it downloads the pages to a computer and generates on the computer a duplicate of what was marked on the paper. Another currently available physical arrangement of the system is that the pen is cordless, includes a transmitter, and downloads to a remote computer a record of the marks on the page when the "magic box" on the page is marked. The computer can optionally optical character read (OCR) any written text or can convert marks on a particular area of the paper (as checks on a form with check boxes or handwriting in a data entry box) to electronic data indicating the selection or information recorded on the form.

One problem that remains with a system based on this technology is how to associate a particular handwritten record with a particular patient. Often, a busy physician does not fully or legibly record patient information such as a full name, a social security number, a patient number, or other unambiguous recordkeeping information identifying a unique patient in his or her initial notes. The physician may later have doubt respecting which patient corresponds to which notes, in this situation. The doubt respecting which patient is the correct one will ordinarily increase as time elapses, so it is important to identify and match a record that lacks identifying information with the appropriate patient in a timely manner.

Another problem in the art is how to communicate detailed discharge instructions to a patient after the patient has been treated.

Modern hospitals find it necessary to discharge patients as soon as possible, which means that they are often sicker and require more information that they can take with them after they are discharged from the hospital than would have been true years ago. Often, the physician is not available at the time of discharge, and even if available may not have the time to prepare custom written instructions-giving the patient exactly the needed information.

Hospitals and physicians have addressed this problem in the past by giving patients preprinted, generalized stock instructions based on the general nature of the complaint leading to hospitalization. Such instructions are general in nature, and may contain much the patient does not need to know and too little of the specific information the patient should know.

Still another problem in the art is how to minimize the time required to properly prepare a medical record reflecting the work done to diagnose and treat the patient. Medical diagnosis requires the routine collection of many different kinds of data reflecting the patient's condition, such as body temperature, blood pressure, the presence or absence of many different disease symptoms, etc. The physician then focuses mainly on the abnormal data—what is wrong with the patient—to reach a diagnosis. Once data is determined to be normal, it has little role in the diagnosis.

Since for most patients most of the data is normal at any given time, much of the data collected turns out not to bear on the problem at hand. Yet, to maintain a proper, unambiguous medical record, it is important to record all of the normal data too, as normal data shows the basis for ruling out a wide variety of possible diagnoses. Recording all the normal data requires a lot of professional time, which is valuable and scarce. Another problem in the art is how to communicate to a clinical user that it is important to document findings specifically intended to avoid ambiguity which encourages litigation, such as normal findings.

One technique that has been developed for addressing this problem is charting by exception. When one is charting by exception, normal data is not charted, and those reading the chart assume that all normal data was in fact collected and found to be normal, although it is not explicitly recorded.

One problem with charting by exception is that many people are reluctant to believe that data that has not been recorded has actually been measured. For example, many nurses have traditionally been trained to assume that anything not charted has not been done. Also, insurance companies often pay different amounts for medical services, depending on what work was done, and may question whether all the normal results implied by charting by exception were actually observed.

Another problem with charting by exception, particularly for physicians who have some discretion to decide how they will evaluate a patient, is that different physicians may normally collect different data while evaluating the patient. Charting by exception assumes that an established schedule of data has been evaluated, and that if some item of the established schedule is normal, it is not explicitly charted. If a medical professional does not check one or more established items, and charting by exception is applied, a false assumption will be made that the professional has checked the omitted item. On the other hand, if a particular professional routinely collects data beyond the established schedule (which may be justified, for example, by a medical discovery not yet reflected on the standard chart or the experience of the physician that additional information would be useful), an assumption will be made that this additional data was not collected. In this case, the medical record is less complete than it should be.

Therefore, a continuing problem in the art is how to reduce the amount of time required to record normal data that has been collected, while maintaining a full and correct record of the data collected in the course of diagnosing and treating the patient.

SUMMARY OF THE INVENTION

One aspect of the invention is apparatus for associating an electronic patient record with the corresponding patient. For this purpose, "direct patient identification data" is data recorded on a patient identification field, selected from one or more names of the patient and one or more codes designating the patient. "Indirect patient identification" can be anything, other than direct patient identification data, that helps to identify which patient corresponds to the record, such as the time the record was written, names or other identifying data not recorded in the proper field, complaint, symptom, diagnosis, treatment room, test ordered, related family member, associated digital photograph, etc. The indirect patient identification data can also be selected from one or more items of medical complaint data, one or more items of symptom data, one or more items of diagnosis data, or combinations of these. An example of the use of more than one item of indirect data is a patient that complains of shortness of breath and is diagnosed with pneumonia. This correlation of a complaint and a diagnosis would distinguish this patient from another patient that complains of shortness of breath but has not been diagnosed with pneumonia. One use of the invention is to reduce or eliminate the ambiguity in definition of the patient corresponding to the medical record.

The apparatus includes a data processor, a display, and a choice input.

The data processor is programmed to do several things. It accesses an unassociated patient record not associated with a unique person. It identifies direct or indirect patient identification data (or both) stored in the unassociated patient record. The data processor accesses a database of at least one known patient record unambiguously associated with a known patient. It compares the direct or indirect patient identification data from the unassociated patient record to corresponding data in the known patient record to identify a set of one or more known patients that correlate with the direct or indirect patient identification data.

The display of this invention displays the set of one or more known patients. A choice input is provided for matching, from the display of members of the set, a member associated with the unassociated patient record. Thus, the previously unassociated patient record is matched or associated with a particular patient. The record can then be used in any manner, such as by storing it as a portion of the particular patient's medical record.

Another aspect of the invention is a method for associating an unassociated patient record with the corresponding patient. This method can include the following steps.

An unassociated patient record not associated with a unique person is accessed. Direct or indirect patient identification data stored in the unassociated patient record is identified. A database of at least one known patient record unambiguously associated with at least one known patient is accessed. The direct or indirect patient identification data from the unassociated patient record is compared to corresponding data in the known patient record to identify a set of one or more known patients that correlate with the direct or indirect patient identification data.

The members of the set of one or more known patient are displayed, and one of those members connected with the unassociated patient record is selected to correspond to the patient record.

Still another aspect of the invention is apparatus for providing customized patient discharge instructions. This apparatus includes an electronic patient record and a discharge instruction format.

The electronic patient record is stored in a data storage medium, and contains data about one or more of, for example, the patient's personal information, complaints, symptoms, medical history, or diagnosis.

The discharge instruction format is also stored in a data storage medium, which may be the same as or different from the previously mentioned data storage medium. The discharge instruction format includes general instructions to be given all patients, or all patients having a particular complaint, and having at least one customizable field for patient-specific instructions to be inserted.

A database is provided relating information in the electronic patient record to patient-specific discharge instructions to be added to the customizable fields. A data processor is used for revising the discharge instruction format by querying the database to identify patient-specific instructions and inserting the patient specific instructions in one or more of the customizable fields, thereby producing patient-specific discharge instructions.

An output device is provided for outputting the patient-specific discharge instructions in a form the patient can read or otherwise use.

Yet another aspect of the invention is a medical chart template adapted to facilitate charting by exception. The template can be configured as a paper form, an image on a computer display, or in any other suitable format. The template includes a multiplicity of recording areas (defined here as at least three recording areas) for entering predetermined categories of data reflecting the patient's condition. The template also has a charting by exception recording area. An entry can be made in the charting by exception recording area for indicating that at least one predetermined category of data on the template is normal if no entry has been recorded in the corresponding recording area indicating an abnormal result. In one embodiment of the invention, the charting by exception recording area is a position-encoded surface-that can detect and transmit to a medical charting system an indication that the charting by exception recording area has been marked.

Still another aspect of the invention is an electronic medical charting system including a data processor. The data processor is programmed to review at least one predetermined recording area of a template including a charting by exception area. The data processor identifies any of the predetermined recording areas where no data has been entered, and makes a record that the corresponding data is normal.

An important advantage realized in certain embodiments of the invention employing position-encoded paper as a charting medium and a digital pen that collects data reflecting where the form is marked and what marks are made is that, from the point of view of the medical professional who is recording patient information, this is the traditional pen-and-paper system and does not require any fundamental change in the tools used for recording patient information. The position-encoded paper on which the charting is done allows a very compact format which still is able to prompt input in all of the appropriate areas of a patient's care. The usual medical abbreviations, short-hand legends, and visual cues can be printed on the form to keep the format compact but still readable and usable by the medical professional. (This prevents the problem of large complex forms.) From the point of view of someone reading the finished chart, the marks on the template can be converted to English-language notations which convert the abbreviations, visual cues, etc. to a more readable form which is more readily understood by medical professionals, as well as medically untrained personnel who have occasion to review the medical record.

DETAILED DESCRIPTION OF THE INVENTION

The following discussion relates to specific aspects of the inventions described in the Summary section of this specification, and various embodiments and alternatives that are contemplated. The following disclosure should be understood to exemplify the invention. The inventions described here are not limited by the particular described embodiments and alternatives.

Associating a Medical Record with the Corresponding Patient

Figure 1:
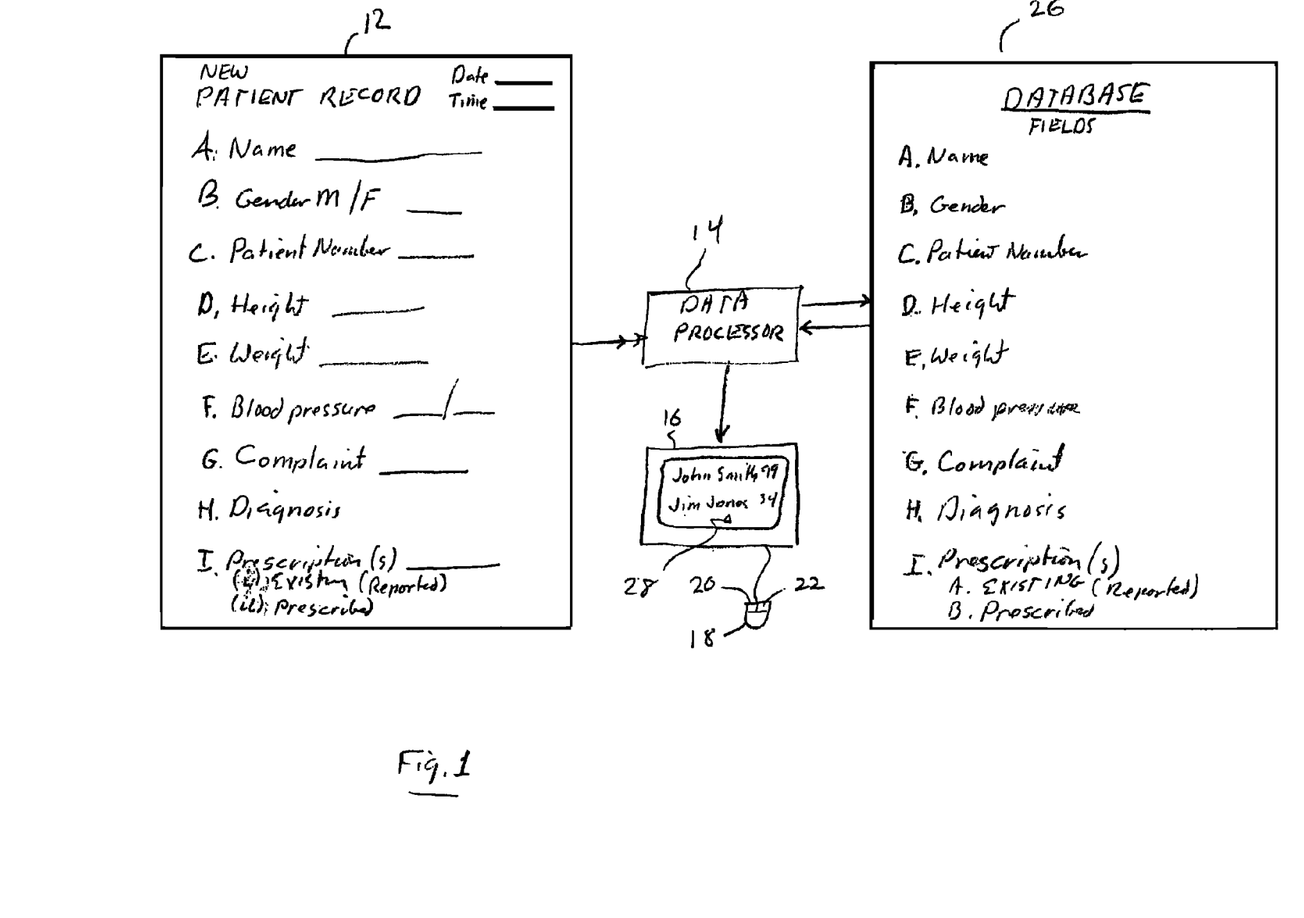
FIG. 1 is a schematic view of the present apparatus for associating a patient record of an unknown patient with information allowing determination of the identity of the patient.

Referring to the drawing figures, one aspect of the invention is apparatus generally indicated at 10 for associating an electronic patient record generally indicated at 12 with the corresponding patient, and for other purposes as further explained below. One use of the invention is to reduce or eliminate the ambiguity in definition of the patient corresponding to the medical record 12.

Figures 3, 4:
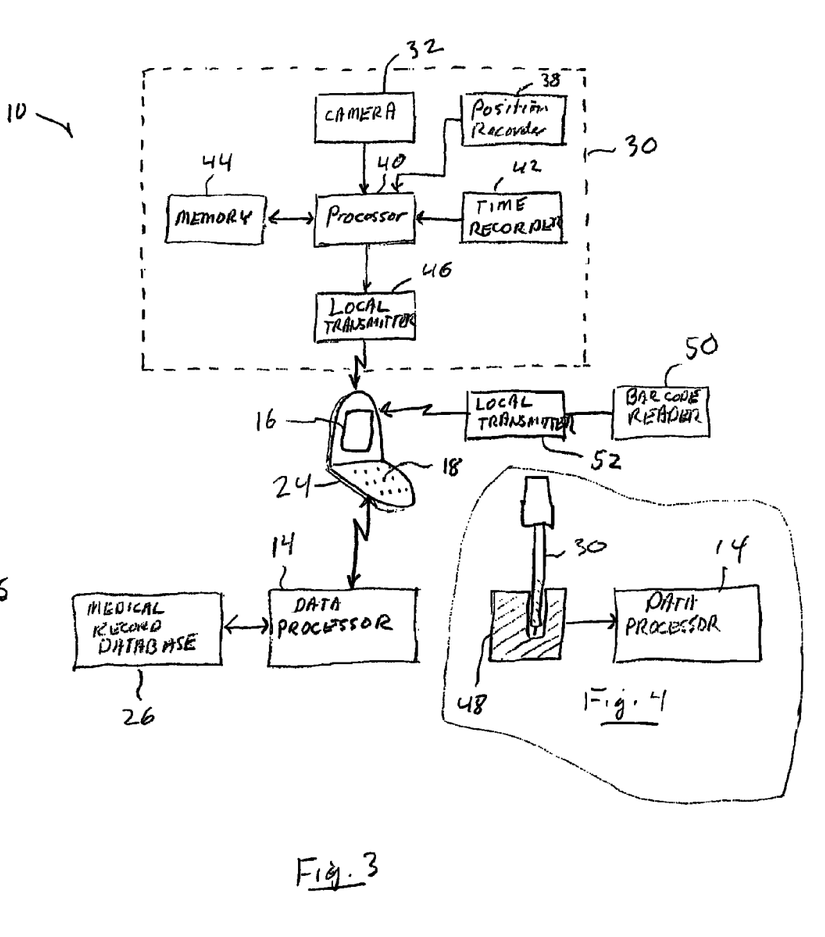
FIG. 3 is a schematic view of apparatus for transmitting data recorded by the camera of FIG. 2 and by a bar code reader, via a cell phone, to a data processor.
FIG. 4 is a diagrammatic view, partially in section, of the pen of FIG. 2 received in a docking station connected to a data processor, for downloading camera data from the pen.

The apparatus includes a data processor 14, a display 16, and a choice input 18. In the apparatus of FIG. 1, the display 16 is a conventional computer display, such as a cathode ray tube or an LCD display, and the choice input 18 is a mouse with input buttons 20 and 22 that are respectively the usual left and right mouse buttons, used to register left and right "clicks" to select information on the display 16. In the apparatus of FIG. 3, the display 16 is the LCD display of a cell phone 24, and the choice input 18 is the keyboard of the cell phone. Any other suitable data processor, display, and choice input may also be used, and the specific choice of equipment or software serving as the data processor, display, and choice input is not significant, in a broad aspect of the present invention.

Referring to FIGS. 1 and 3 in particular, the data processor 14 is programmed to do several things. It is operatively connected (directly, as by a wire link, or indirectly, as via a transmitter/receiver link) to, and therefore is equipped to access, an unassociated patient record 12 not associated with a unique person. It identifies direct or indirect patient identification data (or both) stored in the unassociated patient record. For example, in FIG. 1, the record 12 is shown to have date and time fields, as well as representative fields A-I of information that is intended to be recorded during the examination of a patient. The illustrated fields are:

A. Name
B. Gender M/F
C. Patient Number
D. Height
E. Weight
F. Blood pressure (systolic/diastolic)
G. Complaint
H. Diagnosis
I. Prescription(s):
  (i) Existing (reported)
  (ii) Prescribed Of the above, items A and C are "direct patient identification data," as they are a name of the patient, a code such as the patient number, or other information either directly identifying a unique patient or at least greatly reducing the number of patients that may share identical such data, and are information that is normally used to distinguish a single person from others.

Some examples of direct patient identification data are a first name, a surname, a middle name, a nickname, a pseudonym, a name suffix like "junior" or "III", a combination of two or more of the above data, a patient number, a social security number, a photograph, a signature, a fingerprint, body scan data, a cell phone number (which usually is associated with a specific person who possesses the telephone, unlike a land line home or business telephone number that might be shared by several or many people and is thus indirect patient identification data), patient wristband data, combinations of these, or other information. The definition of direct patient identification data includes types of direct patient information not expressly listed above.

Items B and D-I and the date and time fields above are examples of "indirect patient identification," as they do not specifically name the patient, but are attributes of the patient or historical information (like the treatment time or where the patient was treated) that may help to identify which patient corresponds to the record. The fields A-I and date or time fields are by no means exhaustive, and can include additional items or exclude some or all of the representative listed items.

Some additional examples of indirect patient identification data in addition to the information in FIG. 1, are medical history data, age data, symptom data, patient physical description data (in addition to height and weight, color of eyes or hair, type of hair (curly, straight, receding hairline, etc.) skin pigmentation, ethnic features, etc. Other pertinent information includes patient location data (such as in what examining room the patient was examined or where the patient is presently), time of treatment data, direct or indirect identification data for a person accompanying the patient, attending medical personnel data, patient address data, patient telephone number data, patient e-mail address data, patient insurance data, patient clothing data (such as the type or condition of the patient's clothing or other wearable items, including shoes and jewelry), patient skin marking data (such as visible moles, freckles, lesions, scars, tattoos, sunburn, tan lines, etc.), data identifying a person accompanying the patient, data concerning relatives of the patient (mother's name, number of siblings, etc.), any combination of these, or other indirect patient identification information. Additional such information will readily be identified by those skilled in the medical arts. The definition of direct patient identification data includes types of indirect patient information not expressly listed above.

The data processor 14 is operatively connected (directly or via a transmitter/receiver link) to, and therefore is equipped to access, a database 26 of at least one known patient record unambiguously associated with a known patient. For example, this database might be information about the patients present in the hospital on the same day as the unknown patient, based on intake and triage data. The database 26 might also be the medical records for the health care facility generally. In FIG. 1, the database 26 has fields A-I, which in this embodiment are the same as the fields on the electronic patient record 12. The database fields can be more or less extensive than illustrated, to any degree, and need not have one-to-one correspondence with the fields on the electronic patient record 12.

The data processor 14 compares direct or indirect patient identification data from the unassociated patient record 12 to corresponding data in the database 26 of known patient records to identify a set of one or more known patients that correlate sufficiently with the direct or indirect patient identification data. The set of patients identified by the data processor can be variously defined, depending on rules programmed into the data processor.

For example, in one embodiment, each field of data in the database 26 corresponding to one or more fields containing information in the patient record 12 can be compared to the patient record 12, with each corresponding field contributing equally to the degree of correlation between the unknown patient forming the subject of the record 12 and the known patients forming the subject of the database 26. Additionally, the fields of data in the patient record 12 can be prioritized to select more important selection criteria and less important selection criteria. For example, direct patient identification data, like one or more names and the patient number, can be relied upon first or given the greatest weight, and data that is likely to change even for the same person on the same day, such as blood pressure, can be given lower weight, or only considered when an identification to the necessary degree of certainty cannot be made from the direct patient identification data presented on the unassociated patient record 12. Some criteria may not be particularly useful for identification of the patient. For example, if a large proportion of the patients have gray hair, gray hair would not be a very specific identifier of a particular patient, while red hair, if infrequent in the patient population, would be a very specific identifier.

As a more detailed example, if the unknown patient has the first name William, is male, and complains of chest pain, the database 26 can be queried to find how many patients share these characteristics. If there is exactly one patient in the database 26 having all of these characteristics, then there is a high probability that the one patient having these characteristics is the same person as the unknown patient. The database can be further queried to determine whether the proposed corresponding patient in the database 26 has other characteristics corresponding or not corresponding to those of the unknown patient. If there are no non-corresponding characteristics, then the match is an easy one, and the set of potential matches is the one person. If there are any non-corresponding characteristics, then the probability that the match is correct goes down, as the data in the database may be erroneous or the unknown patient may not correspond to any entry in the database 26. In this case, the set of possible patients might be defined as those known patients having the greatest number of common attributes with the unknown patient. The fact that there is non-correlating data, and the amount or nature of such data for each member of the set, can also be displayed.

If there is more than one patient having particular queried characteristics, then data can be associated with each member of the set of possible patients, indicating the odds that each member on the list is the correct one. Weights can be given to each type of data, and all the patients identified in the database 26 can be ranked by combining the weights of the corresponding items of data. For example, assume that 1000 patients are cataloged in the database 26, and assume that 30 of those patients are named William, 15 of those patients have red hair, and 25 of those patients were admitted to the emergency room using this system on the same day as the unknown patient in the record 12. One weighting system would be to weight each factor according to the number of patients in the database 26 that share the characteristic, and thus the probability that any particular member of the group sharing that characteristic is the correct choice. These three probabilities can then be combined by multiplying 30/1000 by 15/1000 by 25/1000 to obtain the probability that any particular patient in the database 26 is not the unknown patient. The result is about 1 chance per 100,000. In one embodiment of the invention, that probability could be assigned to the name of each patient having red hair, named William, and treated on the day in question. The possible matching individual members of the set could then be prioritized according to the calculated probability that each said member of the set should be associated with the unassociated patient record. The probability calculated for each member of said set could be displayed in connection with (such as next to) each name offered as possibly being the unknown patient. In a simple version of this, the identifying data could be displayed along with the matching data or unmatched data leading to the assignment of each name in the set of patients possibly associated with the record 12. In addition, the number or proportion of patients in the database 26 having the same characteristic could be added to the display 16 to give the reader an indication of how unique the particular characteristic is in the database.

The names and, optionally, probabilities associated with one or more known patients can then be displayed on the display 16 for review by the physician who made the record 12, or by another person who is matching the record 12 to a particular patient.

A choice input 18 is provided for matching, from the display of members of the set, a member associated with the unassociated patient record. In FIG. 1, the mouse 18 is the choice input, and it can be manipulated to put the cursor 28 over the name chosen by the person manipulating the mouse, then the selection button 20 or 22 can be clicked, optionally once, to enter the selection. Thus, the previously unassociated patient record 12 is matched or associated with a particular patient. The apparatus can be programmed to accept a single click of the mouse button or other selection switch, while said pointing device is positioned in proximity to a displayed patient identity, as agreement that the selected patient identity is that of the patient identified in said unassociated record.

The record 12 can then be used in any manner, such as by adding it to the database 26 or otherwise incorporating it in the chosen patient's records.

Another aspect of the invention is a method for associating an unassociated patient record with the corresponding patient. This method can include the following steps, which here correspond to the operations of the apparatus described above, although the same apparatus can also be used in a different manner.

An unassociated patient record is accessed. Direct or indirect patient identification data stored in the unassociated patient record is identified. A database of at least one known patient record unambiguously associated with at least one known patient is accessed. The direct or indirect patient identification data from the unassociated patient record is compared to corresponding data in the known patient record to identify a set of one or more known patients that correlate with the direct or indirect patient identification data.

The members of the set of one or more known patient are displayed, and one of those members connected with the unassociated patient record is selected to correspond to the patient record.

Figure 2:
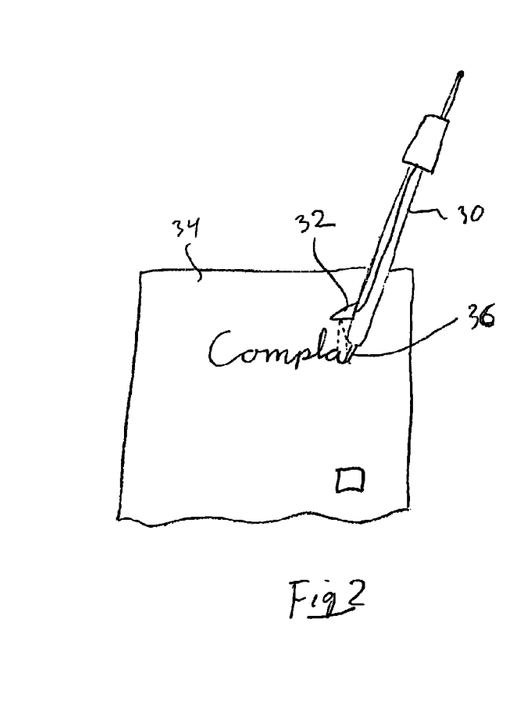
FIG. 2 is a diagrammatic perspective view of a record being made on encoded paper by a pen having a digital camera for periodically storing an image of the encoded paper in the locality of the writing tip of the pen.

A more specific apparatus which can optionally be used for making and storing the record 12, and identifying the patient to whom the record refers, is described in FIGS. 2 and 3. A digital encoder 30, shown in the form of a writing instrument in FIG. 2, and functionally in FIG. 3, is provided for capturing the unassociated patient record 12 and transmitting the record to an appropriate medical record system for processing and entry into patient records.

The digital encoder 30 includes a digital camera 32 for capturing a close-up image from an adjacent position-encoded surface 34. The camera can be programmed to periodically record an image, forming a series of images. The position-encoded surface can be, for example, the glyph-encoded paper described in U.S. Pat No. 6,502,756. The series of images captured by the digital camera 32 represents the path of movement of the encoder 30 in proximity to the position-encoded surface. In alternative embodiments, the digital encoder 30 could also be a touch screen or tablet computer or PDA screen on which data is directly handwritten, or a scanner recording an image previously handwritten on paper or another medium. An advantage of using the position-encoded surface 34 is that it can be provided in the form of a seemingly ordinary paper tablet or notebook which is lightweight and easily carried and used by physicians and others, and yet the data can be saved and, optionally, transferred in electronic form immediately as it is generated.

In yet another contemplated embodiment, the digital encoder 30 can be fitted with accelerometers to record the accelerations and decelerations of the encoder 30 on the surface of paper 34 or another medium, which in this case would not need to be position-encoded. The electronic accelerometer data can be used to reconstruct the motion of the encoder 30 on the surface 34, thus again allowing reconstruction of the handwriting formed on the surface 34. In still another embodiment, the digital encoder 30 can be constructed with a writing ball (as in a ball-point pen) equipped with rotation detectors, like the ball on a mouse, so its motion can be converted to electronic data again representing handwriting undertaken with the encoder 30.

In the embodiment of FIG. 2, the digital encoder 30 includes a marking instrument 36 positioned for marking the position-encoded surface 34 as the encoder is moved in proximity to the position-encoded surface 34. The use of a marking instrument makes the use of the encoder 30 intuitive to the user, who uses the encoder 30 exactly like a traditional pen to mark paper. At the same time, by marking the position-encoded surface 34, the user is making a personal record of his or her observations, which can be saved and later consulted in the event there is a need to re-enter the information (as when the power source, not shown, of the encoder 30 is exhausted or disconnected or transmissions as described below are unsuccessful, incomplete, or include errors).

Refer now to FIG. 3, where the digital encoder 30 of FIG. 2 is shown in the form of a block diagram. In this embodiment the digital encoder further comprises a position recorder 38, a processor 40, a time recorder 42, a memory 44, and a local transmitter 46.

The position encoder 38 can be operatively connected to the processor 40 to add to the unassociated patient record 12 data indicating where the digital encoder 30 is located while it is being used to record data in the unassociated record. For example, the position recorder 38 may be a receiver that is fed by a local radio signal generated in a particular medical examination room, identifying the room.

Alternatively, the position recorder 38 can be configured as a second function of the camera 32, which can take an image of a unique feature of the examination room, such as a bar code on the door of the room, to identify the position of the encoder 30 at that time, and can take an image of a unique feature of the patient's identification bracelet to identify the person who is the subject of the medical record 12 at the time the record is made. The digital encoder 30 thus can serve as apparatus for associating a patient with an electronic record, including an identification device for addressing an on-patient identifier to identify the patient and a handwriting encoder that makes an electronic record of handwriting as it is written.

Knowing in what examination room the encoder 30 was used and for what patient the encoder 30 was used at a given time can strongly correlate the record 12 to the particular patient and examination room.

The time recorder 42 can be operatively connected to the processor 40 to add to the unassociated patient record 12 time-of-day or date data (or both) indicating when the digital encoder is being used to record data in the unassociated record. Knowing the exact time the record was made can correlate the record 12 to a patient treated at the recorded time.

The processor 40 can build the image data from the camera 32, the position data from the recorder 38, and the time data from the recorder 42 into a patient record 12, and store the record 12 in the memory 44. Plural records can be formed and stored in the memory 44, then deleted as confirmation has been received that the record has been entered in the electronic medical records of the pertinent medical facilities.

One or more medical records 12 stored in the memory 44 can be recalled and transmitted via the local area transmitter 46, one current example of which is a Bluetooth™ transmitter, to a suitable location, such as a cell phone 24 carried by the examining physician, or alternatively a receiver built into the examination room (not shown). The cell phone transmitter can be used to relay the record 12 to a remote data processor 14, or the data processor can be built into the cell phone 24 in another embodiment. In still another embodiment, the cell phone 24 can be replaced by a push-technology e-mailing device, such as a Blackberry® e-mail communicator, which can be programmed to periodically e-mail a record 12 to a remote data processor 14.

In the embodiment of FIG. 3, the data processor 14, the medical record database 26, the display 16, and the choice input 18 can function much like the corresponding parts of FIG. 1, except that the choice input 18 could either be used to input a number or to highlight and click on a particular line of the display 16 representing a particular patient selected from the patient set written on the display 16.

FIG. 3 shows another expedient for recording the presence of a particular patient in a particular examination room, at a particular time, to assist the correlation of the patient records transmitted by the encoder 10 with the identity of the patient. In this embodiment a bar code or proximity reader 50 is provided, which optionally is fixed in an examination room or on its door or doorframe by a tether, or by securing it within the room, as by bolting it to a wall. The reader 50 is used to read a bar code or other suitable marking or transmitter on a patient identification bracelet, a medical professional identification badge, or the like. The reading data can be transmitted via a local area transmitter 52 to the cell phone 24, or is transmitted via a data line or other communication path also permanently located within the examination room. The reader 50 can also add to the transmitted record the time of transmission and the location or identity of the reader 50, so the patient location, time, and identity can be matched. This correlation can also be performed by providing an RFID (radio frequency identification) device in the physician's identity badge and/or the patient's identity bracelet, which then can associate one or more of the physician, patient, treatment room, a particular data encoder 30, and the time and date of treatment in a single record. A conventional RFID is a passive transmitter; it utilizes the energy content of a signal received from the RFID reader to power its transmitter. A suitable reader can be located in each examination room or other treatment area to keep a running record of the locations of patients and/or medical personnel whenever one of the RFIDs is in proximity to a reader.

FIG. 4 shows another alternative embodiment of the invention, in which the digital encoder 30, instead of or in addition to transmitting data to the processor 14 via the transmitter 46 and cell phone 24, can be placed in a docking station or cradle 48, which uploads the records 12 created since the previous docking to the data processor 14.

In the apparatus of FIGS. 3-4, the data processor 14 can include optical character recognition programming to extract data from writing in the unassociated patient record 12. Such programming is primarily useful to identify block characters written in the record, like alphanumeric characters written one-to-a-box in a series of uniform boxes that constrain the writer to write well-formed characters. The data processor also can include handwriting recognition programming to extract data from handwriting in the unassociated patient record 12. Three basic types of data can be identified, potentially: (1) the words written by the writer, which are determined by decoding handwriting into the corresponding text characters; (2) pictorial data, such as a sketch made or marks on a standardized drawing that is a pre-printed part of the record; and (3) the identity of the writer, identified by finding unique characteristics of the writer's handwriting, much like one person can often recognize who has written a handwritten notation, if the reader is familiar with the handwriting of the writer. This can either be done by analyzing the handwriting itself, or by providing force sensors that determine the characteristic pressure put on the encoder 30, or how tightly the encoder 30 is being gripped, or the angle at which the encoder 30 is held by the writer while writing.

Customized Discharge Instructions

Figure 5:
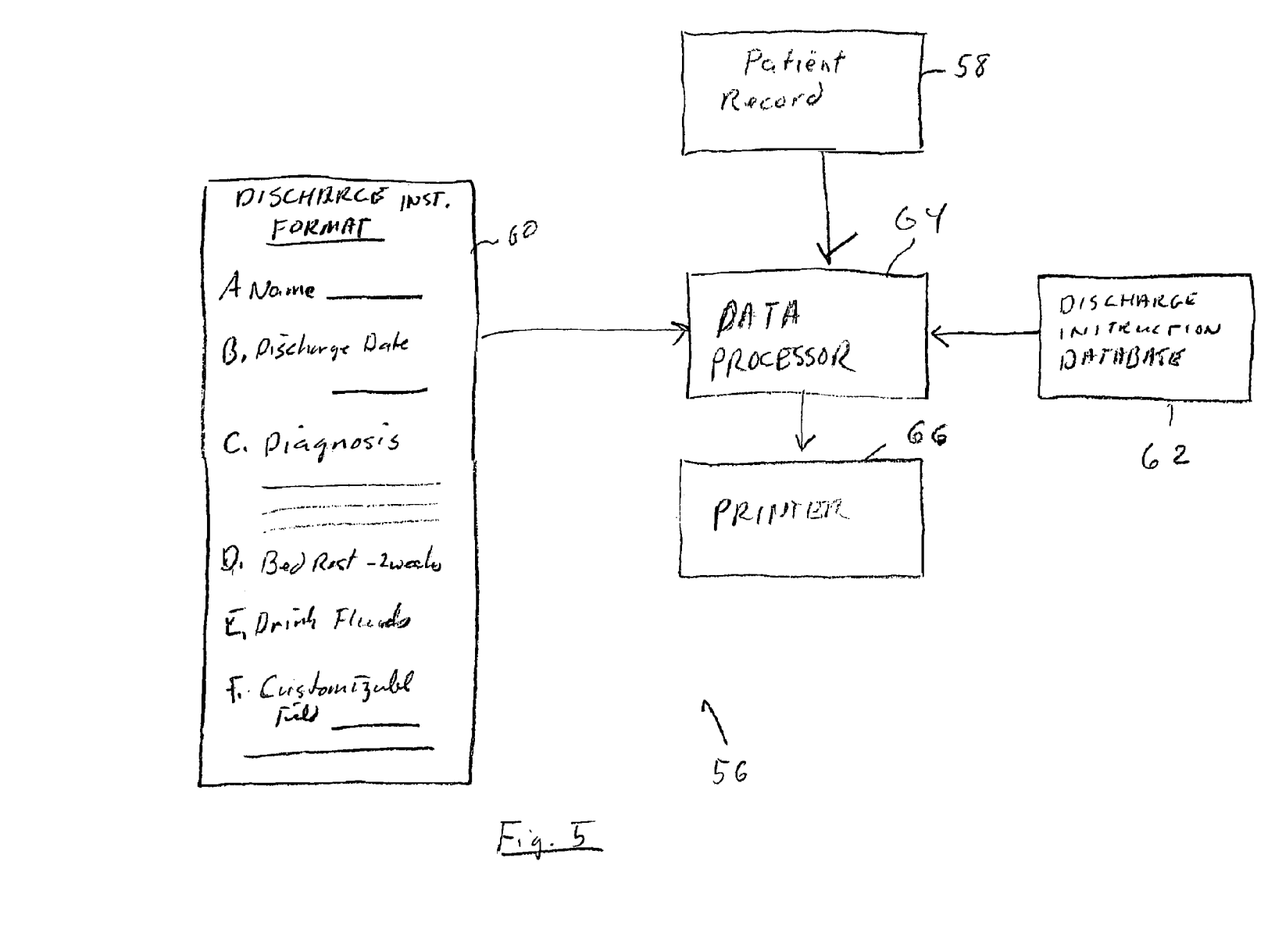
FIG. 5 is a schematic view of a system for preparing health care facility discharge instructions, customized to the situation of a particular patient.

Referring now to FIG. 5, still another aspect of the invention is apparatus generally indicated at 56 for providing customized patient discharge instructions. This apparatus includes an electronic patient record 58 and a discharge instruction format 60.

The electronic patient record 58 of a known patient is stored in a data storage medium, and contains data about one or more of, for example, the patient's personal information, complaints, symptoms, medical history, or diagnosis.

The discharge instruction format 60 is also stored in a data storage medium, which may be the same as or different from the previously mentioned data storage medium. The discharge instruction format includes general instructions to be given all patients, or all patients having a particular complaint, and having at least one customizable field for patient-specific instructions to be inserted, here represented by the field F shown in the format 60. The format 60 also contains conventional fields A-E presenting predetermined information or instructions.

A discharge instruction database 62 is provided, also stored in a data storage medium, which may be the same as or different from the previously mentioned data storage medium. The database 62 relates information in the electronic patient record 58 to patient-specific discharge instructions to be added to the customizable fields. A data processor 64 is used for revising the discharge instructions provided by the format 60 by querying the database 62 to identify patient-specific instructions and inserting the patient specific instructions in one or more of the fields A-F, thereby producing patient-specific discharge instructions.

An output device is provided, such as a printer 66, for outputting the patient-specific discharge instructions in a readable format.

One non-limiting example of information to put in the customizable field F is data in the patient record 58 respecting how to live with a post-discharge disability. Patient-specific discharge instructions can instruct the patient in detail how to change daily activity to live successfully with the disability. An example of a conventional instruction that might be handed out to any patient diagnosed with glaucoma might be: "You have been diagnosed with glaucoma. Glaucoma results from an abnormally high pressure in the eye. Glaucoma can cause loss of peripheral vision with sparing of central vision.

Therefore, if all other aspects of your ocular health are normal, then 20/20 vision is still achievable. To prevent further damage to your eyes, you should use the eye drops that have been prescribed for you. With more advanced cases of glaucoma, the peripheral vision can be significantly reduced, resulting in tunnel vision to the point where driving is no longer possible."

A customized instruction would take into account patient-specific information, such as which eye it is in, how advanced it is in the particular patient, etc. For example, a customized version of the above instruction might read as follows: "You have been diagnosed with advanced glaucoma in the left eye, and early stages of glaucoma in the right eye. Glaucoma results from an abnormally high pressure in the eye. In your case, on Jul. 20, 2003, when you visited our emergency room complaining of loss of peripheral vision, we measured the pressure in your eyes and found it to be x psi in excess of normal pressure in your left eye and y psi in excess of normal pressure in your right eye. Glaucoma can cause loss of peripheral vision with sparing of central vision. Because all other aspects of your ocular health are normal, 20/20 vision may still be achievable in your right eye. To prevent further damage to your eyes, you should use the EYESAVE, 30% solution eye drops that have been prescribed for you, in both eyes, in the morning when you get up and after dinner. You told us on Jul. 20, 2003, that you last had your eyeglasses prescription updated about three years ago. In view of your diagnosis, you should make an appointment with your regular optometrist or ophthalmologist to obtain prescription glasses or other eyewear that is right for a patient who has glaucoma. Since you have advanced glaucoma in your left eye, your peripheral vision to the left is significantly reduced, from a normal value of 100 degrees to 30 degrees, resulting in tunnel vision to the point where we must instruct you not to drive an automobile or truck until you install a special mirror on the left side of your vehicle to correct for your tunnel vision."

Note that the instruction not to drive without a special mirror on the left side is based on the diagnosis of the extent of loss of peripheral vision and which eye is affected. Other conditions affecting driving, alone or cumulatively, that might be put into the instructions might include, for example, limitations of eyesight, hearing, coordination, reaction time, depth perception, alertness, or memory.

Such an instruction would be far more useful for the particular patient, as well as providing more patient satisfaction with the level of care provided and documentation that the patient was warned about the practical effects of the diagnosis, what medication was prescribed, how to use it, etc. The instruction would also be useful to other health professionals treating the patient, so they would understand exactly what the physician found and recommends. The discharge instructions could also contain all pertinent instructions, in the event the patient has more than one condition that was diagnosed or treated. Additionally, the discharge instructions could be integrated with preexisting instructions to the patient, based for example on previous diagnoses of chronic conditions. The instructions could also list all the medications that are currently prescribed for the patient, to serve as a checklist. A daily schedule could be laid out stating the times to take each medication, in relation to the time of day and meals. This could be a sort of "owner's manual" for the patient.

Thus, when the physician orders discharge instructions to be prepared, they would be prepared for the particular patient, in view of that patient's diagnosis, automatically.

Charting by Exception Option

Figure 6:
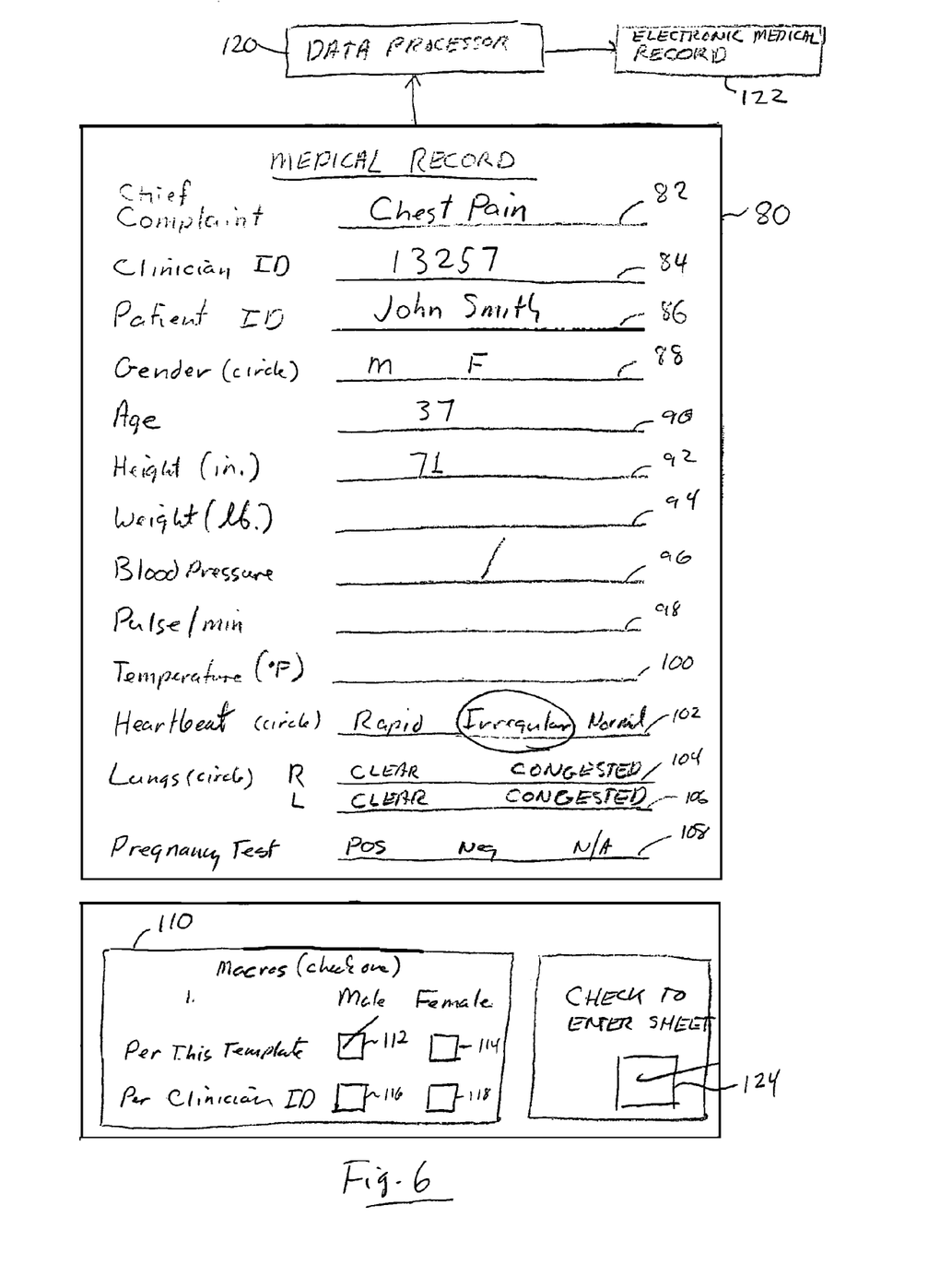
FIG. 6 shows a medical record template including a charting by exception recording area, operatively connected to a data processor that uses the template to construct a corresponding electronic medical record.

Referring now to FIG. 6, a simplified medical record template 80 is shown having a recording area 82 to enter the chief complaint, a recording area 84 for the examining physician or other clinician to identify herself, a recording area 86 to identify the patient, and a multiplicity of data recording areas such as 88-108 for entering predetermined categories of data reflecting the patient's demographic information and the presence or absence of all potentially pertinent symptoms. The template 80 also has a charting by exception recording area 110.

The position encoded surface can contain a visual language tailored to documentation context (in this case medical) which creates synergism between the documenting clinician, the visual language, and the documentation produced. For example, the words "review of systems" can be placed on a page in a specific way with a specific surrounding set of characters and colors which can be grasped intuitively by the clinician to mean "all other systems reviewed and our negative except for the above documentation." The charting by exception recording area can be marked to express this meaning in English on the electronic medical chart to which data from the template is added. Normally the interpretation of such documentation is difficult for someone not trained in the visual language. The invention, however, allows for the conversion of such a visual language to human readable English.

While the template 80 can be printed on position-encoded paper and used as described above, the same system can be implemented using any of the previously described hardware or other expedients known to those skilled in the art. While a simplified template is shown, the same invention has application to the more complicated, detailed templates commonly used with current electronic medical documentation systems.

The macro recording area 110 can be used for entering an indication that at least one predetermined category of data on the template is normal, unless an entry other than normal has been recorded in the corresponding recording area. For example, in the illustrated embodiment, the clinician has the opportunity to select from four macros: 112 for a male patient, instructing a report of all un-entered data on this template as normal; 114 for a female patient, instructing a report of all un-entered data on this template as normal; 116 for a male patient, instructing a report of whatever un-entered data is pre-selected by this clinician as normal; and 118 for a female patient, instructing a report of whatever un-entered data is pre-selected by this clinician as normal.

The "per clinician ID" choices give the clinician the option to customize the electronic report resulting from his use of this form to his own practice. Customization can be in the direction of reducing the set of un-entered information on the form reported as normal (which normally would be less preferred, as it is commonly important to document everything listed on the form). The customization feature can also allow the clinician to add additional data, not called out on the form, to be reported.

The system optionally can be configured so that, if a particular physician has not customized the medical chart entries to be made for his work, checking one of the "per clinician" boxes provides the same customization, in that instance, as checking the "per this template" box, so a complete medical record will be made even if the clinician has called for customization that has not been implemented. The template 80 can also have a legend on it, or be printed along with a legend page, or itself be customized in each data recording area that is affected by a standard or custom macro, indicating what customization the physician has selected, so the physician will have at hand the details of her customization.

For one example, a particular clinician may be in the habit of always asking patients if a parent or siblings has had a similar complaint in the past. The physician can customize the form by instructing that if a "per clinician" macro is selected on a form she fills out, the electronic medical record should report that the patient indicated that his parents and siblings have not reported a similar complaint in the past. If parents or siblings have had a similar complaint in the past, the clinician can enter that information, not called out on the template, in a free text area of the form, or by a separate report.

The "per this template" choices give the clinician the option to prepare a report in the standard format, entering as normal all items not completed on the form.

The clinician can choose one way or the other each time the form is used, depending on the particular patient situation.

FIG. 6 also shows an electronic medical charting system comprising a data processor 120 programmed to review at least one recording area from the areas 94-108 of the template 80 after a macro from the recording area 110 has been marked, identify any of the recording areas such as 94-108 where no data indicating abnormality has been entered, and make a record in the electronic medical record 122 that any predetermined category of data not entered as abnormal is normal.

For example, in FIG. 6, the clinician put data in the recording areas 82, 84, 86, 90, 92, and 102, did not positively respond in the recording areas 88, 94-100, 104, 106, and 108, and checked the "per this template—Male" macro in the macro area 110. The clinician then checked the "Check to enter sheet" box 124, which in this embodiment (position-encoded paper written upon by a pen incorporating a digital camera) caused the medical template system to upload to the data processor 120 the data and instructions entered by marking the template 80.

The data processor 120 is programmed to enter the data from the completed recording areas 82, 84, 86, 90, 92, and 102, in the chosen format, in the electronic medical record 122. The data may be entered in the same format as the template 80, or in a different format, such as a narrative report providing the data in the form of ordinary English phrases or sentences, optionally eliminating abbreviations and unnecessary text. The data processor 120 also carries out the instructions indicated by the macro 112 selected by the clinician. This may be done by adding to the electronic medical record 122 the nominal entries for a male patient corresponding to the recording areas 88, 94-100, 104, 106, and 108. The resulting medical record, in this instance expressed in the same form as the template 80, may be as shown in FIG. 7.

Figure 7:
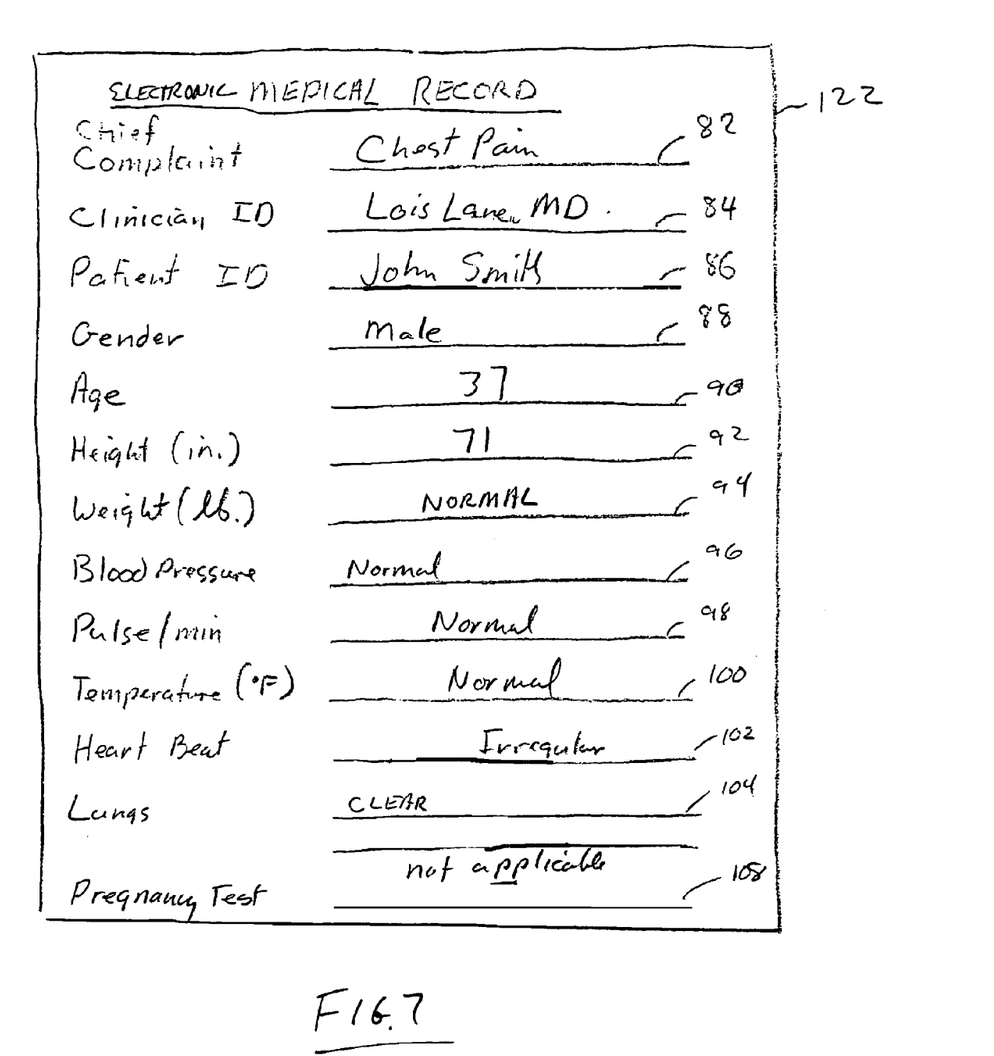
FIG. 7 shows the electronic record resulting from the entries shown in FIG. 6, after application of one embodiment of the present invention.

FIG. 7 shows data in the recording areas 82, 84, 86, 90, 92, and 102, as indicated by the clinician. The data can be converted to a more readable form, as in this embodiment, by expedients such as filling out the clinician's name instead of an identification number in the area 84, and by eliminating the alternatives not selected ("rapid" and "normal") in the area 102.

FIG. 7 also shows data entered in the recording areas 88, 94-100, 104, 106, and 108 of the electronic medical record 122, where the clinician did not mark specific information in the template 80. In the area 88, the data processor 120 responded to a mark on the "Per this Template—Male" macro 112 by entering that the patient was a male. "Male" was spelled out and "F," standing for the un-selected choice "female," was suppressed to enhance readability. In the recording areas 94-100, the data processor responded to the clinician's mark in the macro 112, and the absence of direct marks in the recording areas 94-100, by indicating the patient's condition as "normal" in the areas 94-100 of the electronic medical record 122. Readability was enhanced in the recording area 96 by reporting the blood pressure simply as "normal," instead of separately reporting the systolic and diastolic pressures by number or as normal.

For the recording areas 104 and 106 of FIG. 6, allowing separate indications for the state of the patient's right and left lungs, the absence of marks by the physician on the template 80, as shown in FIG. 6, and the selection of the macro 112, caused the data processor to enter in area 104 in the electronic record 122 that the patient's lungs were "clear" (their nominal condition in a healthy patient). This entry was simplified by combining the reports for the right and left lungs as a single word in the area 104, and by suppressing the legend and response for the area 106. Had the physician reported that the left lung was congested and the right lung was clear, or had the physician reported that the left lung was congested and made no remark about the right lung, the data processor 120 could be programmed to separately report the condition of each lung in the record 122.

In the recording area 108 relating to pregnancy, which was not marked by the physician examining a male patient in the template 80 of FIG. 6, the data processor responded to the absence of markings in the recording area 108, and the selection of a "male" template 112, to note that pregnancy is not applicable in this situation. "Not applicable" was written out and un-selected responses were suppressed, in this embodiment, for readability. Alternatively, the "pregnancy test" legend and the recording area 108 could be eliminated entirely in the electronic medical record 122 generated by the data processor 120 for a male patient.

In the template 80 in FIG. 6, if the patient were female, the customization might differ respecting the recording area 108 for pregnancy. The nominal condition would optionally be "not pregnant," instead of "not applicable" for the male patient. Alternatively, as outlined further below, the recording area 108 for pregnancy might be reserved as not subject to customization for a female patient. Thus, selecting the macro 114 instead of 112 would result in different reporting and different permissible options for customization in the area 108.

In the illustrated medical charting system, certain predetermined categories of data identified by the data processor can be customizable while others are not. For example, it may be useful to provide one or more areas such as the clinician ID in the area 84, the patient name in the area 86, or the patient's age in the area 90 that are not customizable. The rationale for preventing customization of the clinician ID is that the clinician ID determines who is responsible for the medical record, and may trigger the entry of data suitable for one clinician but not another. For another example, there usually is no "nominal" patient name or patient age, and this information is important to positively identify which medical record should be updated with the information recorded on the template 80. Other data, as illustrated previously, is useful to customize. The data processor 120 can be programmed not to accept customizing instructions for certain data recording areas of the template 80.

The medical charting system can also be configured to give different medical professionals different levels of authorization to enter instructions by selecting a macro. For example, a nurse might be given the ability to customize the data recording areas 88, 92, 94, 98, and 100, based on information in the recording area 84 indicating that a nurse entered the data. A nurse commonly can be given this authority because it will commonly be obvious to the physician who subsequently examines the patient that the patient is male or female per the area 88, tall, short, or in between per the area 92, or normal in weight or obese or malnourished per the areas 92 and 94. Thus, any significant mistake in these areas by the nurse will be evident, and will not cause the physician to misdiagnose the patient. Also, a nurse may routinely be the only one to check the patient's weight, height, pulse and temperature, and is well versed in what is normal or not in these routine areas.

Other areas, such as the condition of the heartbeat in the area 102 and condition of lungs in the area 104, might be reserved so only a physician can customize them, as only the attending physician might normally evaluate these symptoms.

Still other areas, such as pregnancy test results, might be reserved only for laboratory professionals who carry out the pregnancy test, so the physician or other medical professionals cannot report the result using a macro. The system can also be arranged so the attending physician cannot enter a result for pregnancy for a female patient even manually, since this finding would normally require a laboratory report.

The system can further be arranged so, for a male patient, a physician can enter a "not applicable" result for pregnancy, either directly or using a macro, but the system will not report in the electronic medical record 122 a positive result for a pregnancy test. Also or instead, the data processor 120 can be programmed to signal to the physician or other personnel in some fashion that inconsistent data (such as "male" and "pregnant") has been entered in the fields 88 and 108 or in the fields 108 and 112 of FIG. 6, for example.

Another contemplated variation is that one medical professional in training or at a lower level, such as a medical student, might be authorized to fill out the data recording areas such as 82-108 of the template 80, but not be authorized to use the macros 112-118. A supervising physician might have authority, after reviewing the template 80 as completed by the medical student, to use the macros. This review system can be facilitated by adding a separate clinician authorization recording area for the macro area 110.

The result of the invention is that the medical record 122 can be complete and readable, without requiring the physician to mark all the here-unimportant details explicitly when filling out the template 80. The physician can focus on reporting the abnormal data that leads a physician to her diagnosis. Also, unlike the traditional "charting by exception" reporting, in which no entry was made to indicate normal data, in the present system entries are made positively indicating that the normal data is normal. The reader is thus reassured that the normal data was in fact collected, as there are no gaps in the explicit written record. Further, providing macros to complete the entry of a large volume of data that has no importance in a particular diagnosis reduces the file size of data requiring uploading to the data processor 120 from the digital pen used to record the information on the template 80. The upload can thus be performed more quickly, more frequently, or more reliably.

What is claimed is:

1. An electronic medical charting system comprising:
 a user interface presenting a medical chart template, the medical chart template comprising:
  a plurality of recording areas configured to enable a user to enter predetermined categories of data reflecting a patient's condition; and
  a charting by exception recording area configured to enable a user to enter an indication that at least one predetermined category of data on the medical chart template has been reviewed, and is normal, unless an entry other than normal has been recorded in the corresponding recording area for said at least one predetermined category;
 a data processor programmed to, when the indication is entered in the charting by exception area:
  review at least one predetermined recording area of the medical chart,
  identify a recording area of said at least one predetermined recording areas where no data indicating abnormality has been entered, and
  make a record that a predetermined category of data corresponding to the identified recording area is normal.

2. The medical charting system of claim 1, wherein the at least one predetermined category of data identified by said data processor is customizable based on an identifier of a physician.

3. The medical charting system of claim 2, wherein a plurality of sets of predetermined categories are defined.

4. The medical charting system of claim 3 wherein said data processor selects a particular set of predetermined categories in a given instance based on information indicating an identity of a medical professional who entered data in at least one of the plurality of recording areas of said medical chart template.

5. The medical charting system of claim 3, where said data processor selects a particular set of predetermined categories in a given instance based on information indicating an identity of a medical professional who entered data in the charting by exception recording area.

6. The medical charting system of claim 3, where said data processor selects a particular set of predetermined categories in a given instance based on the indication made in the charting by exception recording area.

7. The medical charting system of claim 1, wherein the medical chart template further comprises:
 a plurality of charting by exception recording areas, each charting by exception recording area being respectively associated with a different set of at least one predetermined category of data on the medical chart template to be entered as normal unless an entry has been recorded in the corresponding recording area.

8. The medical charting system of claim 1, where said charting by exception recording area comprises a position-encoded surface.

9. The electronic medical charting system of claim 1, wherein the data processor is further adapted to:
 identify a second recording area of said at least one predetermined recording areas where data indicating abnormality has been entered; and
 make a record that a second predetermined category of data corresponding to the identified second recording area is abnormal.

10. The medical charting system of claim 1, wherein:
 the charting by exception recording area comprises a plurality of input fields each configured to receive input indicating that at least one predetermined category of data on the medical chart template has been reviewed, and is normal, unless an entry other than normal has been recorded in the corresponding recording area for said at least one predetermined category; and
 different predetermined categories are associated different input fields of the plurality of input fields.

11. The medical charting system of claim 10, wherein: the plurality of input fields comprise an input field associated with a male patient and an input field associated with a female patient.

12. The medical charting system of claim 10, wherein: the plurality of input fields comprise an input field associated with a user of the system; the at least one predetermined category associated with the input field associated with the user are customized by the user.

13. A method of recording medical information on an electronic medical record for a patient, the method comprising:
- providing a user interface comprising a medical chart template, the template comprising:
  - a plurality of recording areas configured to enable a user to enter predetermined categories of patient data reflecting a condition of the patient; and
  - a charting by exception recording area configured to enable the user to indicate that at least one predetermined category of patient data on the template has been reviewed, and is normal when no entry is made in a corresponding recording area of the plurality of recording areas;
- receiving through the user interface an entry in each recording area of a first set, the first set comprising recording areas of the plurality of recording areas and each entry indicating that a predetermined category of data corresponding to the recording area is abnormal;
- entering in the electronic medical record, with at least one processor, for each recording area in the first set, information based on the entry received in the recording area, the information documenting the abnormality in a correspond category of the predetermined categories of patient data;
- receiving through the user interface an indication in said charting by exception recording area that predetermined categories of data that have not been documented on the medical chart template as abnormal should be documented as normal; and
- based on the indication received in said charting by exception recording area, entering in the electronic medical record, with at least one processor, for each recording area in a second set, information indicating normal data in a correspond category of the predetermined categories of patient data, the second set comprising recording areas of the plurality of recording areas for which there is received no entry indicating that a predetermined category of data corresponding to the recording area is abnormal.

14. The method of claim 13, wherein:
the user interface comprises a position encoded surface; and
said plurality of recording areas are areas of the position encoded surface.

15. The method of claim 14, wherein said receiving steps comprise receiving from a marking instrument configured to mark on said position-encoded surface with a marking instrument.

16. The method of claim 15, wherein said marking instrument further comprises a data capture device configured to determine what marks have been made in said plurality of recording areas and configured to transmit data reflecting said marks to an electronic medical record system.

17. At least one non-transitory computer readable medium comprising computer-executable instructions that, when executed on at least one processor of a device, perform a method of updating an electronic medical record for a patient, the method comprising:
- receiving through a user interface comprising a medical chart template:
  - first data entered through a first portion of a plurality of recording areas configured to enable a user to enter predetermined categories of patient data reflecting a condition of the patient; and
  - an indication entered through a charting by exception recording area, the indication indicating that at least one category of patient data on the template associated with the charting by exception recording area has been reviewed, and is normal when no entry is made in a corresponding recording area of the plurality of recording areas;
- entering the first data in the electronic medical record; and
- based on the indication received in said charting by exception recording area, entering in the electronic medical record for each recording area associated with the charting by exception recording area for which no entry is made, information indicating normal data.

18. The at least one non-transitory computer readable medium of claim 17, wherein:
the user interface comprises a position encoded surface; and
said plurality of recording areas are areas of the position encoded surface.

19. The at least one non-transitory computer readable medium of claim 18, wherein said receiving steps comprise receiving from a marking instrument configured to mark on said position-encoded surface with a marking instrument.

20. The at least one non-transitory computer readable medium of claim 19, wherein said marking instrument further comprises a data capture device configured to determine what marks have been made in said plurality of recording areas and configured to transmit data reflecting said marks to an electronic medical record system.

21. The at least one non-transitory computer readable medium of claim 17, wherein the computer executable instructions further comprise instructions for:
receiving user input defining the at least one category of patient data on the template associated with the charting by exception recording area.

22. The at least one non-transitory computer readable medium of claim 17, wherein the method further comprises determining the at least one category of patient data on the template associated with the charting by exception recording area based on an identity of a user of the device.

* * * * *